United States Patent [19]
Joo

[11] Patent Number: 5,951,483
[45] Date of Patent: Sep. 14, 1999

[54] METHOD AND APPARATUS FOR DETECTING AN INTERNAL PACEMAKER PULSE

[75] Inventor: Tae Hong Joo, Redmond, Wash.

[73] Assignee: Physio-Control Manufacturing Corporation, Redmond, Wash.

[21] Appl. No.: 09/013,236

[22] Filed: Jan. 26, 1998

[51] Int. Cl.$^6$ .............................. A61B 5/0402; A61N 1/37
[52] U.S. Cl. .............................. 600/509; 600/500; 607/27
[58] Field of Search .............................. 607/27; 600/509, 600/500

[56] References Cited

U.S. PATENT DOCUMENTS

| | | |
|---|---|---|
| 4,527,567 | 7/1985 | Fischler et al. . |
| 4,830,006 | 5/1989 | Haluska et al. . |
| 4,880,004 | 11/1989 | Baker, Jr. et al. . |
| 5,000,189 | 3/1991 | Throne et al. . |
| 5,033,473 | 7/1991 | Wang et al. . |
| 5,074,308 | 12/1991 | Sholder et al. . |
| 5,103,819 | 4/1992 | Baker et al. . |
| 5,144,947 | 9/1992 | Wilson . |
| 5,184,615 | 2/1993 | Nappholz et al. . |
| 5,217,021 | 6/1993 | Steinhaus et al. . |
| 5,231,990 | 8/1993 | Gauglitz . |
| 5,312,447 | 5/1994 | Begemann . |
| 5,312,451 | 5/1994 | Limousin et al. . |
| 5,376,104 | 12/1994 | Sakai et al. . |
| 5,391,187 | 2/1995 | Freeman . |
| 5,447,518 | 9/1995 | Pless . |
| 5,448,997 | 9/1995 | Kruse et al. . |
| 5,488,553 | 1/1996 | Renger . |
| 5,507,778 | 4/1996 | Freeman . |
| 5,545,182 | 8/1996 | Stotts et al. . |
| 5,545,185 | 8/1996 | Denker . |
| 5,660,184 | 8/1997 | Donehoo et al. . |

OTHER PUBLICATIONS

Jussi Tranesjo, Thomas Fahraeus, Mats–Erik Nygards and Ove Wigertz, *Evaluation of New Equipment*, "Automatic Detection of Pacemaker Pulses in Ambulatory ECG Recording," PACE, vol. 5, Jan./Feb. 1982.

*An Ambulatory Recording System for Pacemaker Follow–Up*, H. Ahlfeldt, T. Ahren, M.–E. Nygards, I. Rinqvist, H. Svedlund, A. Walker and O. Wigertz, 1987.

*The Design and Evaluation of a New Hardware Pace Pulse Detector*, Mousa N. Shaya and Barry L. Wyshogrod, 1988.

*Primary Examiner*—William E. Kamm
*Assistant Examiner*—Carl H. Layno
*Attorney, Agent, or Firm*—Christensen O'Connor Johnson & Kindness PLLC

[57] ABSTRACT

A defibrillator (8) is disclosed that analyzes a 12-lead ECG signal of a patient (25) to detect internal pacing pulses generated by an internal pacemaker (26). At least one of the twelve leads, e.g., lead II, is passed through a low pass filter (28) followed by an analog-to-digital converter (16). The digitized lead II signal is then applied to a digital bandpass filter to remove low and high frequency noise. Using the digital, bandpass filtered, lead II signal, a short term energy (s) and a long term energy (r) are computed. The short term energy (s) consists mostly internal pacing pulse energy, while the long term energy (r) essentially consists of the energy associated with background noise. If the ratio of the short term energy (s) to the long term energy (r) is greater than a predetermined threshold, or if the pair of energy values falls within a range of values defined as a function of the predetermined threshold and absolute noise, a pacing pulse is detected.

25 Claims, 5 Drawing Sheets

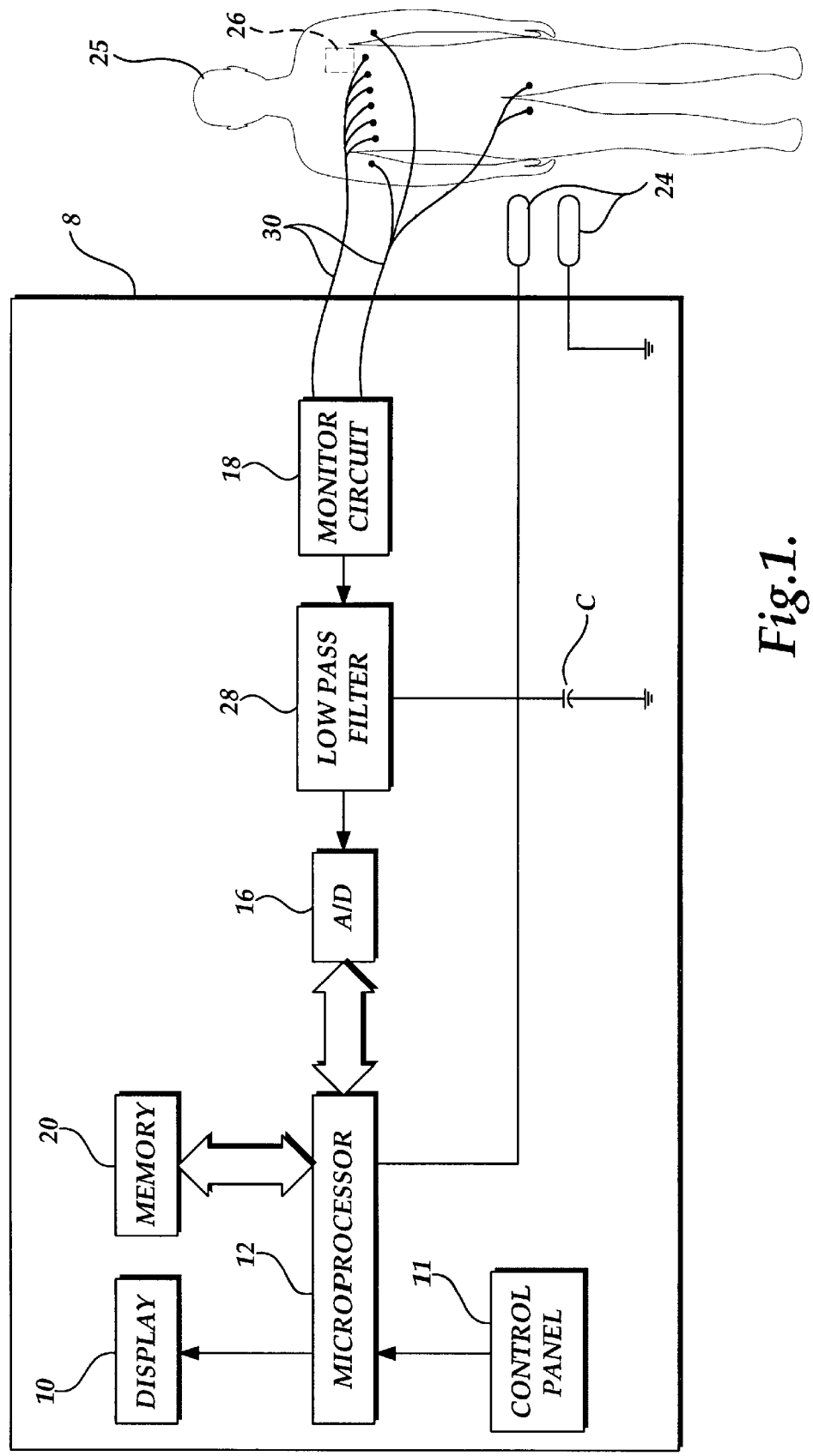

METHOD AND APPARATUS FOR DETECTING AN INTERNAL PACEMAKER PULSE

FIELD OF THE INVENTION

The present invention relates generally to detecting pacing pulses generated by an internal pacemaker, and more particularly, to an external defibrillator/monitor capable of distinguishing an internal pacemaker pulse in an electrocardiogram signal.

BACKGROUND OF THE INVENTION

One of the more common treatments for diseased or damaged hearts which are incapable of producing electrical excitation pulses, i.e., the pulses necessary to begin contraction of the heart's ventricles and atria, is to implant an internal cardiac pacemaker. Internal cardiac pacemakers electrically supply the necessary excitation pacing pulses directly to the heart through a set of electrodes. Such pacing pulses may be applied continuously if the heart is completely malfunctioning, or intermittently if it is only occasionally malfunctioning. Monitoring an electrocardiogram (ECG) signal from a patient having an internal pacemaker is difficult because pacing pulses generated by the internal pacemaker can interfere with the ECG signal and result in misdiagnosis of the heart's condition. For example, when an internal pacing pulse is generated, the QRS complex of the EGG signal is widened, which may falsely indicate acute myocardial infarction (AMI), a heart condition for which active therapy such as thrombolytic therapy is delivered. However, if the pacing pulse were to go undetected, a shockable heart rhythm could be mistakenly diagnosed by a ventricular fibrillation detection algorithm and a defibrillation shock applied. As yet another example, the ECG signal of a patient with an internal pacemaker who is experiencing asystole may contain periodically occurring pacing pulses. However, asystole is the cessation of heart activity and is indicated in the ECG signal by the absence of a QRS complex. Consequently, the presence of the pacing pulse may cause the asystole to go undetected.

Internal pacemakers are now much smaller in size and use far less energy to generate the pacing pulses. Accordingly, the pacing pulses are significantly smaller in both amplitude and duration, making them difficult to detect. It is even more difficult to detect such small pacing pulses in the presence of noise, which may essentially drown out the small pacing pulse entirely. As a result, many known internal pacing pulse detection techniques are no longer adequate for detecting pacing pulses. Hence, the threat of misdiagnosis remains.

Accordingly, a method and apparatus for detecting internal pacemaker pulses which are small in both amplitude and duration are needed. The method and apparatus should detect internal pacing pulses in the presence of noise with acceptable degrees of specificity and sensitivity. Further, the method and apparatus should provide a flexible range of energy values in which to detect a pacing pulse, so that as pacemaker technology advances, and pacing pulses become smaller, the method and apparatus of the present invention remains viable. As explained in the following, the present invention provides a method and apparatus that meets these criteria and solves other problems in the prior art.

SUMMARY OF THE INVENTION

In accordance with the present invention, a method and apparatus are provided for detecting internal pacing pulses generated by an internal pacemaker. The method and apparatus may be employed by any device capable of monitoring an ECG signal, such as a cardiac monitor or defibrillator. Preferably, a 12-lead ECG signal is monitored by the present invention for possible pacing pulses. At least one of the twelve leads is passed through a low pass filter followed by an analog-to-digital converter. The digitized lead signal is then applied to a digital bandpass filter to remove low and high frequency noise. Using the digitized, bandpass filtered signal, a short term energy and a long term energy are computed. The short term energy consists of mostly internal pacing pulse energy, while the long term energy essentially consists of the energy associated with background noise. In one embodiment of the present invention, a pacing pulse is detected if the ratio of the short term energy to the long term energy is greater than a predetermined threshold. In an alternative embodiment, a range of values is defined as a function of the predetermined threshold and absolute noise. Thus, if the ratio of short term energy to long term energy falls within this range, a pacing pulse is detected.

In accordance with other aspects of the invention, the lead used to determine the short term energy and the long term energy is switched if too many pacing pulses have been detected within a predetermined time interval, and another lead may be used to determine the short and long term energies.

An apparatus capable of performing the method described above represents a further aspect of this invention.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 1 is a block diagram of an external cardiac defibrillator capable of detecting internal pacing pulses in accordance with the present invention;

DETAILED DESCRIPTION OF THE PREFERRED EMBODIMENT

Figure 2A:
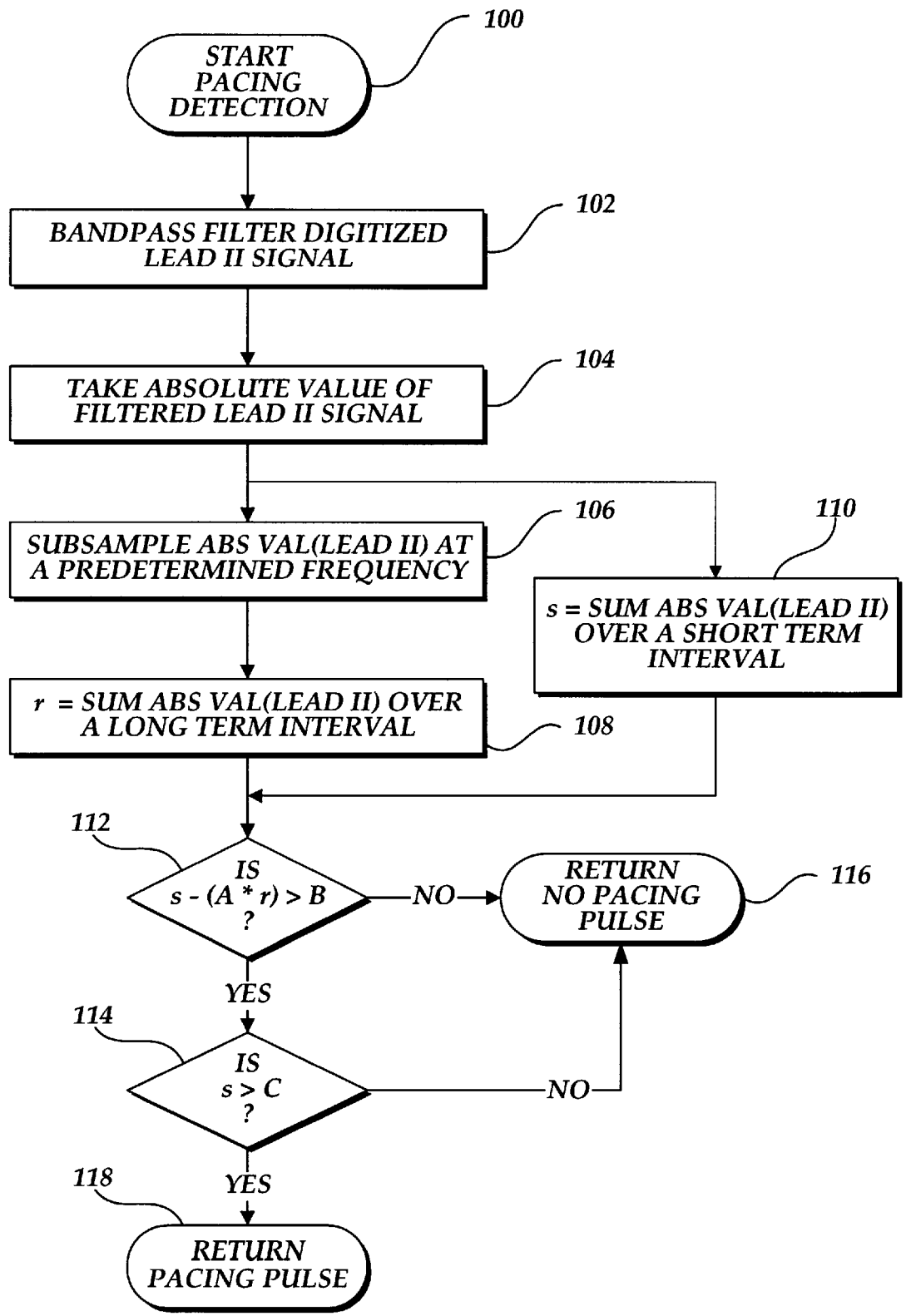
FIGS. 2A and 2B are flow charts illustrating the logic used by the defibrillator shown in FIG. 1 for detecting an internal pacing pulse.

FIG. 1 is a block diagram of an external cardiac defibrillator 8 connected to a patient 25 that is capable of detecting pacing pulses generated by an internal pacemaker 26 in accordance with the present invention. In one embodiment of the present invention, the defibrillator 8 analyzes a 12-lead electrocardiogram (ECG) signal of the patient 25 to identify a shockable heart rhythm and to detect internal pacing pulses. When a shockable heart rhythm such as ventricular fibrillation is identified, the defibrillator 8 stores electric charge and delivers the electric charge to the patient 25 in the form of an electric current pulse, i.e., a defibrillation pulse. The defibrillation pulse is applied to the patient 25 over a set of paddles 24.

Now that the overall operation of the defibrillator 8 has been discussed, the key components of the defibrillator 8 as illustrated in FIG. 1 will be described in more detail. It will be appreciated by those of ordinary skill in the art that the defibrillator 8 may contain more components than those shown in FIG. 1. However, a disclosure of the preferred embodiment of the present invention does not require that all of these general conventional components be shown. It will further be appreciated that the present invention may be implemented by a cardiac monitor having essentially the same components as the defibrillator 8 except that the monitor does not have the components necessary for delivering a defibrillation pulse.

The defibrillator 8 analyzes a 12-lead ECG signal of the patient to identify shockable and non-shockable heart rhythms and to detect internal pacing pulses. The ECG signal is received from a set of ten electrodes 30, i.e., four limb electrodes and six precordial electrodes placed on the patient's limbs and chest. The signals received from the ten electrodes 30 are monitored by a monitoring circuit 18, which processes the ECG signals to derive 12 leads or waveforms. These 12 leads are well known in the art as leads I, II, III, aVr, aVl, aVf and V1, V2, V3, V4, V5 and V6. In one embodiment of the present invention, the ECG signal associated with lead II is used to detect internal pacing pulses. It has been empirically determined that lead II is most likely to be affected by an internal pacing pulse. Since the internal pacemaker 26 applies pacing pulses to either the right atrium of the heart or the left ventricle of the heart, it follows that lead II, which is generated from the right shoulder of the patient to the left leg of the patient and which provides the best view of the inferior portion of the heart, will be most affected by the pacing pulse generated. However, it will be appreciated that the present invention may use any of the other leads in order to detect an internal pacing signal and that, depending on the pacemaker 26 and the internal pacing pulse its generates, another lead may actually be more suitable.

In the actual embodiment of the present invention described herein, the lead II signal is passed by the monitoring circuit 18 through a low pass filter 28 with a cutoff frequency of 3000 Hz. The low pass filter 28 is employed to remove aliasing which can distort the lead II signal. The low pass filtered lead II signal is then provided to an analog-to-digital converter 16 with a sampling rate of 10 KHz. A microprocessor 12 then analyzes the digital lead II signal provided by the analog-to-digital converter 16 in order to detect whether or not the patient's ECG signal contains an internal pacing pulse generated by the internal pacemaker 26.

It will also be appreciated from FIG. 1, that the monitor circuit 18 is connected to an energy storage capacitor C to aid the microprocessor 12 in monitoring the voltage on the energy storage capacitor C as the capacitor is being charged. If a shockable rhythm is detected, the microprocessor 12 charges the energy storage capacitor C to a desired voltage, which in turn prepares the defibrillator 8 to apply a defibrillation pulse to the patient 25 using the paddles 24. The microprocessor 12 is also connected to a display 10 and a control panel 11. Information is entered on the control panel 11 by a defibrillator operator to control the defibrillator. The display 10 indicates to the operator the condition of the defibrillator 8 and the patient 25.

Figure 2B:
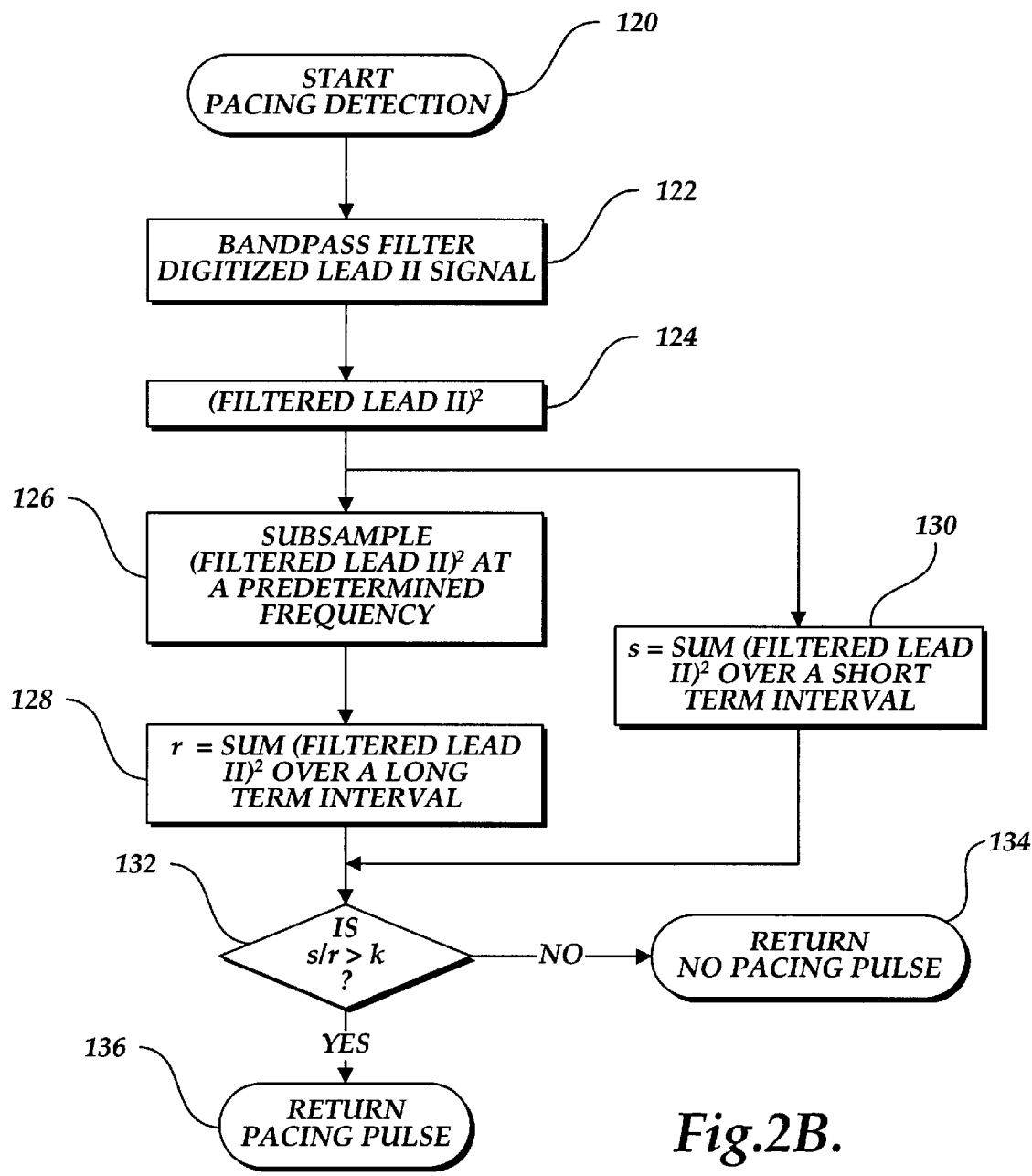

FIG. 2A illustrates the logic used by the microprocessor 12 in an embodiment of the present invention employing a fixed-point processor to evaluate the digital lead II signal to detect an internal pacing pulse. In one embodiment of the present invention, the microprocessor 12 is a fixed-point processor, which requires that all calculations made in order to detect pacing pulses be performed in fixed-point arithmetic. As will be described in more detail below, this impacts the method implemented by the present invention to detect internal pacing pulses. Although a fixed-point processor is desirable from a cost and reduced computation standpoint, those of ordinary skill in the art will appreciate that a floating-point processor may also be used without departing from the scope of the present invention. As illustrated in FIG. 2B and as described in more detail below, a slightly different logic is used if the microprocessor 12 is a floating point processor.

Returning to FIG. 2A, the logic begins in a block 100 and proceeds to a block 102 where the digitized lead II signal is applied to a digital bandpass filter. A bandpass filter is used because the bandwidth of a pacing signal is significantly larger than the bandwidth of an ECG signal. Therefore, the noise and low frequency signals that may be present are removed. In the actual embodiment of the present invention described herein, the bandpass filter is an infinite-duration impulse response (IIR) filter that is based on elliptic function. In the actual embodiment described herein, the bandpass filter passes 300 to 3500 Hz. Because the present invention uses energy in the passband, the nonlinear phase response of the passband filter is immaterial.

Next, the absolute value of the bandpass filtered lead II signal is determined in a block 104. The absolute value of the filtered signal is then used to compute a short term energy and a long term energy associated with the lead II signal. It will be appreciated by those of ordinary skill in the art, that by computing the short term energy and long term energy using the absolute value of the filtered lead II signal, only an approximation of the true short term energy and long term energy are computed. However, the fact that an approximation of these energies is used is immaterial to the detection of an internal pacing pulse. Consequently, the term "energy" will continue to be used in reference to these approximations for ease in explanation.

Returning to a block 110 in FIG. 2A, the short term energy (s) is computed by summing the absolute value of the bandpass filtered signal over a short term interval, e.g., 1 msec. The short term energy is computed based on the assumption that if there exists an internal pacing pulse, the energy present in a signal of a short duration would be mostly due to the pacing pulse, rather than noise or some other factor, whose energy value cannot be quantified or is unknown. The duration of the short term interval is determined to be 1 msec in the actual embodiment described herein because the main lobe width of the output of the bandpass filter is about 1 msec for a conventional narrow-width (0.1 msec) pacing pulse.

In parallel with the computation of the short term energy, the long term energy associated with the lead II signal is determined. More specifically, in a block 106 the absolute value of the lead II signal is subsampled at a predetermined rate, e.g., a factor of 10. In a block 108, the long term energy (r) is computed as the sum of the absolute value of the subsampled, bandpass filtered lead II signal over a long term interval, e.g., 50 msec. The long term energy is essentially a measurement of the background noise being experience by the system. The long term energy is computed based on the assumption that the energy associated with the internal pacing pulse will average out over the long term interval and thus, will not significantly impact the measurement of the background noise.

An internal pacing pulse is detected as a function of the short term energy and the long term energy, i.e., if the ratio of the short term energy, which is likely comprised of mostly pacing pulse energy, and the long term energy, which is comprised of mostly background noise, is greater than some predetermined threshold, a pacing pulse must be present. In other words, if a pacing pulse exists, the ratio of the short term energy to the long term energy will be significantly larger than if no pacing pulse exists. This relationship is defined as follows:

$$s/r > k \qquad (1)$$

where (k) is an empirically predetermined threshold. In the actual embodiment of the present invention described herein, the predetermined threshold (k) is empirically determined using the standard measurement for white noise as a starting point.

Since the microprocessor 12 in the actual embodiment of the present invention currently being described is a fixed-point processor, merely computing the aforesaid ratio does not provide sufficient accuracy. Hence, a range or region of short term and long term energy values must be defined in which the ratio of short term to long term energy is likely to fall, and thus, indicate the presence of an internal pacing pulse. In this regard, a pacing pulse is detected when the following two conditions are satisfied:

$$s - (A*r) - B > 0 \qquad (2)$$

$$s - C > 0 \qquad (3)$$

where s and r denote the short and long term energies, and the coefficients A, B and C are empirically determined constants. A is a coefficient having approximately the same value as the predetermined threshold (k). However, the exact value for (k) cannot be accommodated by a fixed-point processor. Thus, another coefficient B is introduced to provide flexibility in determining the coefficient A. Finally, coefficient C is assigned a value representing a measurement of absolute noise, i.e., a minimum level of noise that is being experienced by the system. In the actual embodiment of the present invention described herein, the values for coefficients A, B and C have been empirically determined to be A=0.11, B=4.09 and C=8.19.

Figure 3:
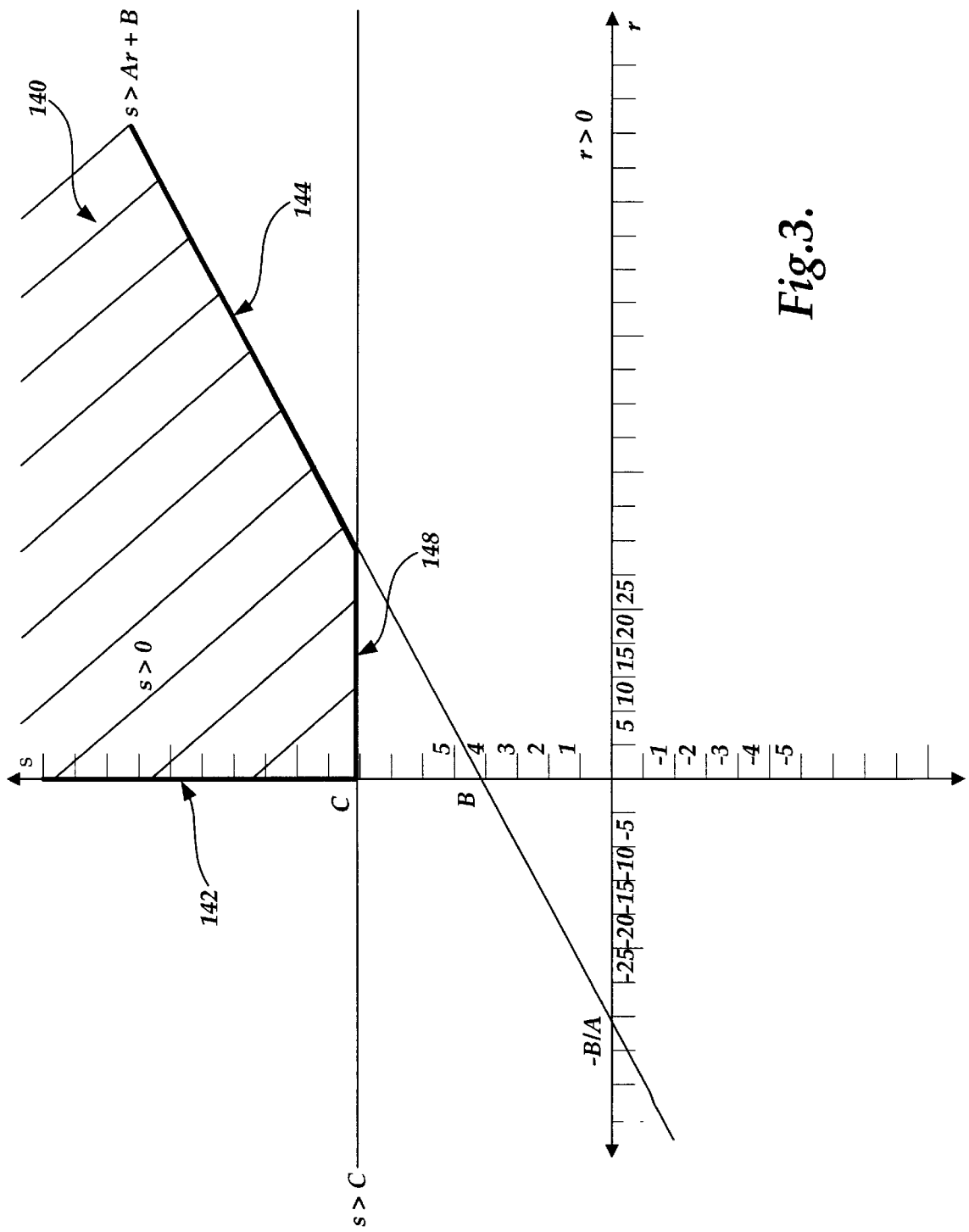
FIG. 3 is a graph illustrating a range of values in which indicate the presence of an internal pacing pulse.

FIG. 3 is a graph illustrating the conditions posed by Equations (2) and (3) and how they define the range of short term and long term energy values which indicate the presence of a pacing pulse. The x axis denotes long term energy values (r) and the y axis denotes short term energy values (s). Hence, the relationship between the short term energy and the term energy defined above in Equation (2) is represented in the graph shown in FIG. 3 as a line 144. The equation for that line is as follows:

$$Ar + B < s \qquad (4)$$

where A is the slope of the line and B is the intercept of the line.

Equation (3) as noted above is depicted in FIG. 3 as a line 148, i.e., s>C. Further, it is a given that both the short term energy (s) and the long term energy (r) are greater than or equal to zero. Consequently, a range or region 140 of short term and long term energy values which indicate a pacing pulse is bound by line 142, line 144 and line 148. In other words, any pair of short term energy and long term energy values that falls within these boundaries indicates the presence of an internal pacing pulse. It will be appreciated from the graph illustrated in FIG. 3 that the coefficients A and B and C can be modified in order to change the range of short term and long term energy values which indicate the presence of a pacing pulse. Hence, increasing the threshold coefficient A will increase the specificity of the pulse detection, i.e., internal pacing pulses will be detected with fewer false alarms. On the other hand, decreasing the threshold coefficient A will increase the sensitivity of the pulse detection, i.e., internal pacing pulses will be detected more frequently, but with greater false alarms.

Returning to FIG. 2A, the logic determines whether or not the pair of long term energy and short term energy values falls within the bounded area 140 in FIG. 3 by first determining in a block 112 if the condition represented by Equation (2) has been met. If not, the pair of short term energy and long term energy values does not fall within the bounded range 140 and a no pacing pulse result is returned in a block 116. However, if the condition of decision block 112 is satisfied, the logic proceeds to a decision block 114 where it determines if the short term energy is greater than the coefficient C, which is the coefficient associated with absolute noise. This condition guards against the case where only noise is present, but the first condition is falsely satisfied. If the result of decision block 114 is negative, a no pacing pulse result is returned in block 116. However, if the results of decision blocks 112 and 116 are both positive, the logic returns a pacing pulse result in a block 118. It will be appreciated that if a pacing pulse is detected, the microprocessor 12 filters out the detected internal pacing pulse from the incoming ECG signals when analyzing the signals for shockable and non-shockable heart rhythms or executing 12-lead ECG interpretation.

As noted above, a slightly different logic is used if the microprocessor 12 is a floating point processor rather than a fixed-point processor. The logic implemented by the microprocessor 12 if it is a floating point processor is illustrated in FIG. 2B. The logic begins in a block 120 and proceeds to a block 122 where the digitized lead II signal is applied to a digital bandpass filter. This is the same digital bandpass filter as described above in connection with block 102 of FIG. 2A. Next, in a block 124, the microprocessor squares the bandpass filtered lead II signal, rather than taking its absolute value. The squared value is used rather than the absolute value since computational precision is not an issue with the floating point processor as it is with the fixed-point processor. In addition, the short term energy and long term energy computed using the squared values are a true computation of energy, rather than an approximation.

In a block 130, the short term energy (s) is computed by summing the squared bandpass filtered lead II signal over a short term interval. In parallel, the long term energy (r) is computed by first subsampling the squared bandpass filtered lead II signal at a predetermined rate, e.g., a factor of 10, in a block 126, and then summing the squared bandpass filtered lead II signal over a long term interval, e.g., 50 msec. Once the short term energy and the long term energy have been computed, the logic proceeds to a decision block 132 where it is determined if the ratio of the short term energy (s) to the long term energy (r) is greater than a predetermined threshold (k) in accordance with Equation (1). Since the microprocessor 12 of this alternative embodiment of the present invention is a floating point processor rather than a fixed-point processor, the computation of the ratio of short term energy to long term energy provides sufficient accuracy for detecting a pacing pulse. Consequently, if the result of decision block 132 is positive, a pacing pulse result will be returned in a block 136. However, if the ratio of the short term energy to the long term energy is not greater than the predetermined threshold, a no pacing pulse result will be returned in a block 134.

It will be appreciated by those of ordinary skill in the art that the predetermined threshold (k) may be adjusted empirically using real data. Higher threshold values will increase specificity and lower threshold values will increase sensitivity. In the actual embodiment of the present invention described herein, the predetermined threshold value is 0.5.

Figure 4:
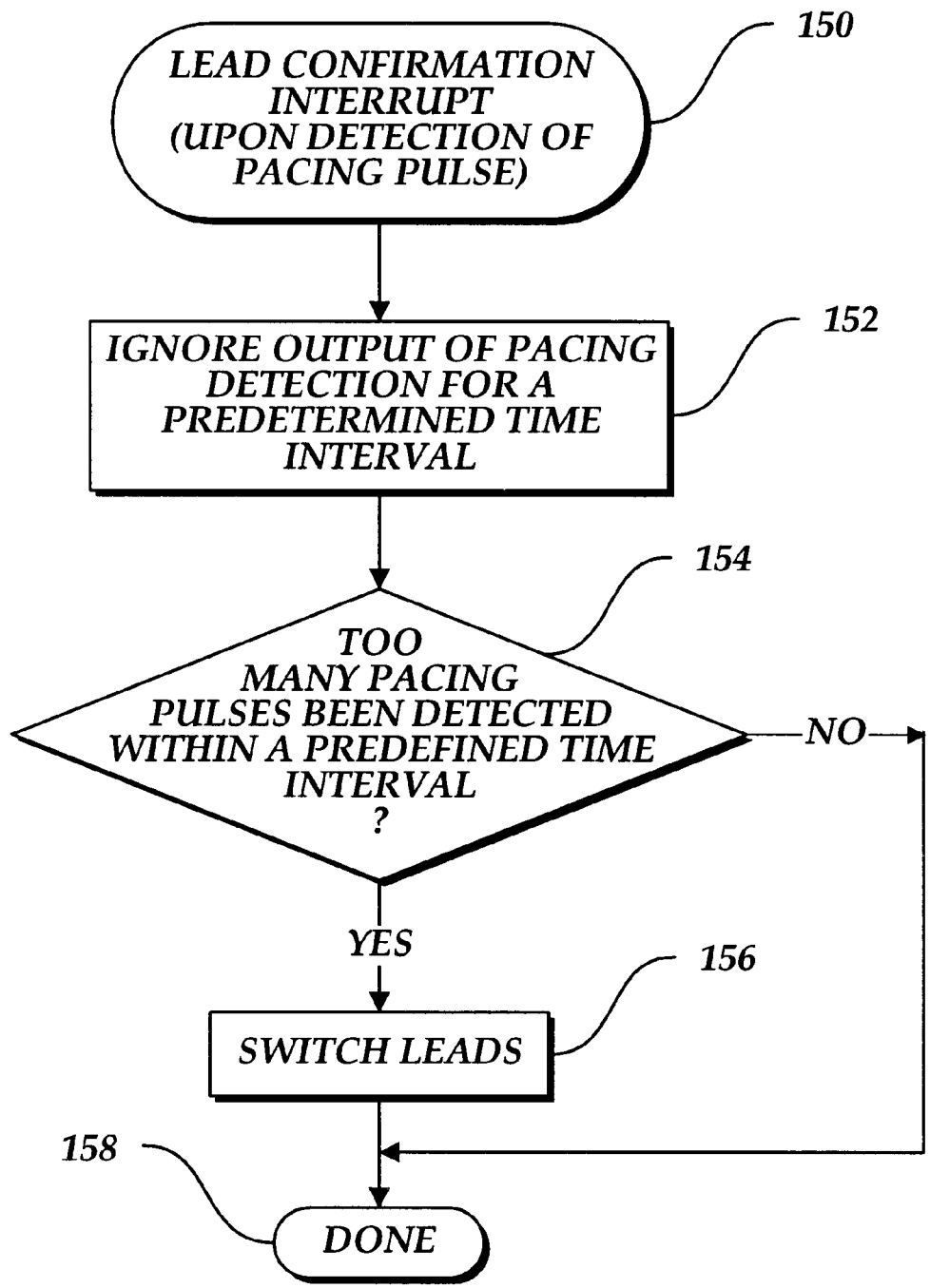
FIG. 4 is a flow chart illustrating the logic used by the defibrillator shown in FIG. 1 to confirm which lead the defibrillator is using to detect internal pacing pulses in accordance with the logic shown in FIG. 2.

As noted above, in the actual embodiment of the present invention described herein, lead II signals are preferably used to determine if an internal pacing pulse is present. However, the lead II information may eventually prove unreliable. Consequently, it is a further aspect of the present invention to confirm the lead it is using to detect internal pacing pulses. The logic employed by the microprocessor 12 to confirm which lead it is using is shown in FIG. 4. The logic begins in a block 150 upon an interruption caused by the detection of a pacing pulse in accordance with the logic shown in FIGS. 2A or 2B. The logic proceeds from a block 150 to a block 152 where the output of the pacing detection routine shown in FIGS. 2A or 2B is ignored for a predetermined time interval in order to avoid multiple detection of the same pacing pulse. In one embodiment of the present invention, the predetermined time interval is 10 msec. In a decision block 154, the logic determines if too many pacing pulses have been detected within a different predefined time interval. For example, in one embodiment of the present invention, the logic determines if more than four pacing pulses have been detected over the last second. Those of ordinary skill in the art will recognize that both the predefined time interval for detecting the pacing pulses and the number of pacing pulses within that time interval that will be tolerated, may be modified for varying pacing pulses without departing from the scope of the present invention.

If too many pacing pulses are detected within the predefined time interval, the lead II signal may be faulty. Accordingly, in a block 156 the microprocessor 12 switches leads and begins using a different lead in order to detect internal pacing pulses. Consequently, the logic shown in FIGS. 2A or 2B will begin analyzing information from a different lead. In one actual embodiment of the present invention, the V4 lead is used. Although the V-leads often do not measure the atria pulses very well, the V4 lead has been empirically determined to collect the most reliable data. However, as noted above, any of the 12 leads may be proven more suitable under certain conditions and thus, the lead confirmation routine shown in FIG. 4 may switch to the more suitable lead. Further, it will be appreciated by those of ordinary skill in the art that it is entirely possible that the microprocessor 12 will continue to switch between lead II and lead V4 if the circumstances so require. In addition, the logic shown in FIG. 4 can be modified so as to switch between any combination or subset of leads. After the lead has been switched in a block 156, the logic ends in a block 158.

While the preferred embodiment of the invention has been illustrated and described, it will be appreciated that various changes can be made therein without departing from the spirit and scope of the invention. For example, any of short term or long term intervals used to compute the short term or long term energies, respectively, may be lengthened or shortened as necessary to fine tune detection to varying pacing pulses. Similarly, the rate at which the digital band-pass filtered signal is subsampled before being used to compute the long term energy, may be increased or decreased as necessary to compensate for microprocessor limitations. Further, the frequencies at which any of the signals are filtered can also be changed in order to compensate for varying pacing pulses or noise levels. Accordingly, it is not intended that the scope of the invention be limited by the disclosure of the actual embodiments described above. Instead, the invention should be determined entirely by reference to the claims that follow.

The embodiments of the present invention in which an exclusive property or privilege is claimed are defined as follows:

1. An apparatus capable of detecting an internal pacing pulse generated by an internal pacemaker, the apparatus comprising:
   (a) a set of electrodes for monitoring twelve lead electrocardiogram signals;
   (b) a processing unit electronically coupled to the set of electrodes to receive twelve lead electrocardiogram signals; and
   (c) a storage medium coupled to the processing unit for storing the twelve lead electrocardiogram signals and program instructions executed by the processing unit that determine whether at least one of the twelve lead electrocardiogram signals includes the internal pacing pulse by:
      (i) determining a short term energy associated with said at least one lead;
      (ii) determining a long term energy associated with said at least one lead; and
      (iii) determining if a ratio of the short term energy to the long term energy is greater than a predetermined threshold value.

2. The apparatus of claim 1, further comprising:
   (a) a filter coupled to the processing unit and the set of electrodes for filtering said at least one lead to remove high frequency signals; and
   (b) an analog to digital converter for digitizing the filtered lead to produce a digitized, filtered lead.

3. The apparatus of claim 2, wherein the program instructions executed by the processing unit further determines whether said at least one lead includes the internal pacing pulse by applying the digitized, filtered lead to a filter to remove low and high frequency signals.

4. The apparatus of claim 3, wherein the storage medium stores program instructions that determine the short term energy by:
   (a) squaring the digitized, filtered lead; and
   (b) summing the digitized, filtered lead over a short term interval.

5. The apparatus of claim 4, wherein the storage medium stores program instructions that determine the long term energy by:
   (a) squaring the digitized, filtered lead; and
   (b) summing the digitized, filtered lead over a long term interval.

6. The apparatus of claim 3, wherein the storage medium stores program instructions that determine the short term energy by:
   (a) taking an absolute value of the digitized, filtered lead; and
   (b) summing the digitized, filtered lead over a short term interval.

7. The apparatus of claim 6, wherein the storage medium stores program instructions that determine the long term energy by:
   (a) taking an absolute value of the digitized, filtered lead; and (b) summing the digitized, filtered lead over a long term interval.

8. The apparatus of claim 7, wherein the storage medium stores program instructions that determine if a ratio of the short term energy to the long term energy is greater than a predetermined threshold value by determining if the ratio of the short term energy to the long term energy falls with a range of values that indicate the presence of an internal pacing pulse.

9. The apparatus of claim 8, wherein the range of values that indicate the presence of an internal pacing pulse is determined based upon the predetermined threshold value and a value representing absolute noise.

10. The apparatus of claim 1, wherein the storage medium stores program instructions that switch to at least one other lead to determine the short term energy and the long term energy if too many internal pacing pulses have been detected within a predetermined time interval.

11. The apparatus of claim 10, wherein said at least one lead is the II lead, and said at least one other lead is the V4 lead.

12. A method for detecting an internal pacing pulse produced by an internal pacemaker, the method comprising:
(a) providing a processing unit for computing and comparing energy values;
(b) computing in the processing unit a short term energy substantially representative of an internal pacing pulse energy;
(c) computing in the processing unit a long term energy substantially representative of noise; and
(d) comparing in the processing unit the short term energy to the long term energy to determine if a significant increase in the short term energy has occurred in comparison to the long term energy.

13. The method of claim 12, wherein comparing the short term energy to the long term energy to determine if a significant increase in the short term energy has occurred comprises computing a ratio of the short term energy to the long term energy and determining if the ratio is greater than a predetermined threshold.

14. The method of claim 13, wherein comparing the short term energy to the long term energy to determine if a significant increase in the short term energy has occurred comprises computing a ratio of the short term energy to the long term energy and determining if the ratio of the short term energy to the long term energy falls with a range of values that indicate the presence of an internal pacing pulse.

15. The method of claim 14, wherein the range of values that indicate the presence of an internal pacing pulse is determined based upon the predetermined threshold value and a value representing absolute noise.

16. A method for detecting an internal pacing pulse produced by an internal pacemaker, wherein the internal pacing pulse is contained in an electrocardiogram signal, the method comprising:
(a) providing a processing unit for determining and comparing energy values;
(b) determining in the processing unit a short term energy associated with at least one lead of the electrocardiogram signal;
(c) determining in the processing unit a long term energy associated with said at least one lead; and
(d) determining in the processing unit if a ratio of the short term energy to the long term energy is greater than a predetermined threshold value.

17. The method of claim 16, further comprising:
(a) filtering said the electrocardiogram signal to remove high and low frequency signals; and
(b) digitizing the filtered electrocardiogram signal to produce a digitized, filtered electrocardiogram signal.

18. The method of claim 17, wherein determining the short term energy comprises:
(a) squaring the digitized, filtered electrocardiogram signal; and
(b) summing the digitized, filtered electrocardiogram signal over a short term interval.

19. The method of claim 18, wherein determining the long term energy comprises:
(a) squaring the digitized, filtered electrocardiogram signal; and
(b) summing the digitized, filtered electrocardiogram signal over a long term interval.

20. The method of claim 17, wherein determining the short term energy comprises:
(a) taking an absolute value of the digitized, filtered electrocardiogram signal; and
(b) summing the digitized, filtered electrocardiogram signal over a short term interval.

21. The method of claim 20, wherein determining the long term energy comprises:
(a) taking an absolute value of the digitized, filtered electrocardiogram signal; and
(b) summing the digitized, filtered electrocardiogram signal over a long term interval.

22. The method of claim 21, wherein determining if a ratio of the short term energy to the long term energy is greater than a predetermined threshold value comprises determining if the pair of the short term energy and the long term energy values falls with a region of values which indicate the presence of an internal pacing pulse.

23. The method of claim 22, wherein the region of values indicating the presence of an internal pacing pulse is determined based upon a function of the short term energy and the long term energy, wherein the short term energy and the long term energy have positive values, and a value representing absolute noise.

24. The method of claim 16, wherein the electrocardiogram signal is evaluated into twelve leads, I, II, III, aVr, aVl, aVf, V1, V2, V3, V4, V5 and V6, and wherein at least one of the twelve leads is used to determine the long term energy and the short term energy.

25. The method of claim 24, further comprising:
(a) ignoring the detection of any pacing pulses for a first predetermined time interval; and
(b) using at least one other lead to determine the short term energy and the long term energy if too many pacing pulses have been detected within a second predetermined time interval.

* * * * *